(12) United States Patent
Lagasse et al.

(10) Patent No.: US 7,811,818 B2
(45) Date of Patent: Oct. 12, 2010

(54) HUMAN LIVER ENGRAFTING CELLS ISOLATED FROM ADULT LIVER TISSUE

(75) Inventors: Eric Lagasse, Pittsburgh, PA (US); Timothy Austin, Morgan Hill, CA (US)

(73) Assignee: StemCells, Inc., Palo Alto, CA (US)

( * ) Notice: Subject to any disclaimer, the term of this patent is extended or adjusted under 35 U.S.C. 154(b) by 170 days.

(21) Appl. No.: 11/502,210

(22) Filed: Aug. 9, 2006

(65) Prior Publication Data

US 2007/0036774 A1    Feb. 15, 2007

Related U.S. Application Data

(63) Continuation of application No. 10/177,178, filed on Jun. 21, 2002, now Pat. No. 7,211,404.

(60) Provisional application No. 60/300,535, filed on Jun. 22, 2001.

(51) Int. Cl.
- C12N 1/08 (2006.01)
- C12N 15/00 (2006.01)
- A61K 48/00 (2006.01)
- A01N 65/00 (2009.01)

(52) U.S. Cl. .................. 435/370; 435/320.1; 424/93.2; 424/93.21; 424/93.7

(58) Field of Classification Search ........................ None
See application file for complete search history.

(56) References Cited

U.S. PATENT DOCUMENTS

| | | | | |
|---|---|---|---|---|
| 5,559,022 | A | 9/1996 | Naughton et al. | 435/240.2 |
| 5,576,207 | A | 11/1996 | Reid et al. | 435/240.2 |
| 5,814,440 | A | 9/1998 | Hill et al. | 435/2 |
| 6,046,036 | A | 4/2000 | Kelley et al. | 435/69.7 |
| 6,069,005 | A | 5/2000 | Reid et al. | 435/325 |
| 6,242,252 | B1 | 6/2001 | Reid et al. | 435/325 |
| 6,242,666 | B1 * | 6/2001 | Sarvetnick et al. | 800/18 |
| 2002/0016000 | A1 | 2/2002 | Reid et al. | |

FOREIGN PATENT DOCUMENTS

| EP | 1 382 672 A1 | 1/2004 |
|---|---|---|
| WO | WO 95/13697 | 5/1995 |
| WO | WO 96/39489 | 12/1996 |
| WO | WO 00/03001 | 1/2000 |
| WO | WO 00/47762 | 8/2000 |
| WO | WO 02/28997 | 4/2002 |

OTHER PUBLICATIONS

Baumann et al., "Expression of the stem cell factor receptor c-kit in normal and diseased pediatric liver: identification of a human hepatic progenitor cell?", *Hepatology*, 30(1):112-117 (1999).
Coleman and Presnell "Plasticity of the hepatocyte phenotype in vitro: complex phenotypic transitions in proliferating hepatocyte cultures suggest bipotent differentiation capacity of mature hepatocytes", *Hepatology*, 24(6):1542-1546 (1996).
Database Medline, Accession No. 1998:445274, *Experimental Cell Research*, 244(1):93-104 (1998).
Douarin, N. M., "An experimental analysis of liver development", *Med. Biol.*, 53(6):427-455 (1975).
Fiorino et al., "Maturation-dependent gene expression in a conditionally transformed liver progenitor cell line", *In Vitro Cell. Dev. Biol. Anim.*, 34(3):247-258 (1998).
Haque et al., "Identification of bipotential progenitor cells in human liver regeneration", *Lab. Invest.*, 75(5):699-705 (1996).
Haruna et al., "Identification of bipotential progenitor cells in human liver development", *Hepatology*, 23(3):476-481 (1996).
Lagasse et al., "Purified hematopoietic stem cells can differentiate into hepatocytes in vivo", *Nat. Med.*, 6(11):1229-1234 (2000).
Lemmer et al., "Isolation from human fetal liver of cells co-expressing CD34 haematopoietic stem cell and CAM 5.2 pancytokeratin markers", *J Hepatol.*, 29(3):450-454 (1998).
Omori et al., "Partial cloning of rad CD34 cDNA and expression during stem cell-dependent liver regeneration in the adult rat", *Hepatology*, 26(3):720-727 (1997).
Palu et al., "In pursuit of new developments for gene therapy of human diseases", *J. Biotechnol.*, 68(1):1-13 (1999).
Petersen et al., "Hepatic oval cells express the hematopoietic stem cell marker Thy-1 in the rat", *Hepatology*, 27(2):433-445 (1998).
Petersen et al., "Bone marrow as a potential source of hepatic oval cells", *Science*, 284(5417):1168-1170 (1999).
Shiojiri et al., "Cell lineages and oval cell progenitors in rat liver development", *Cancer Res.*, 51(10):2611-2620 (1991).
Sprangrude et al., "Purification and Characterization of Mouse Hematopoietic Stem Cells", *Science*, 241:58-62 (1988).
Susick et al., "Hepatic progenitors and strategies for liver cell therapies", *Ann. N.Y. Acad. Sci.*, 944:398-419 (2001).
Tateno et al., "Growth and differentiation in culture of clonogenic hepatocytes that express both phenotypes of hepatocytes and biliary epithelial cells", *Am. J. Pathol.*, 149(5):1593-1605 (1996).
Dandri et al., "Repopulation of mouse liver with human hepatocytes and In Vivo infection with hepatitis B virus", *Hepatol.*, 33:981-988 (2001).
De Boer et al., "Expression of Ep-CAM in normal, regenerating, metaplastic, and neoplastic liver", *J. Pathol.*, 188:201-206 (1999).
Dabeva et al., "Proliferation and differentiation of fetal liver epithelial progenitor cells after transplantation into adult rat liver", *Am. J. Pathol.*, 156:2017-2031 (2000).

(Continued)

*Primary Examiner*—Robert M Kelly
(74) *Attorney, Agent, or Firm*—Mintz Levin Cohn Ferris Glovsky and Popeo, P.C.; Ivor R. Elrifi, Esq.; Christina K. Stock, Esq.

(57) ABSTRACT

A substantially enriched mammalian hepatic liver engrafting cell population is provided. Methods are provided for the isolation and culture of this liver engrafting cell. The progenitor cells are obtained from a variety of sources, including fetal and adult tissues. The cells are useful in transplantation, for experimental evaluation, and as a source of lineage and cell specific products, including mRNA species useful in identifying genes specifically expressed in these cells, and as targets for the discovery of factors or molecules that can affect them.

4 Claims, 13 Drawing Sheets

OTHER PUBLICATIONS

Kubota et al., "Clonogenic hepatoblasts, common precursors for hepatocytic and biliary lineages, are lacking classical major histocompatibility complex class I antigen", *Proc. Natl. Acad. Sci. USA*, 97(22):12132-12137 (2000).

Mitaka, T., "Hepatic stem cells: from bone marrow cells to hepatocytes", *Biochem. Biophys. Res. Commun.*, 281:1-5 (2001).

Suzuki et al., "Flow-cytometric separation and enrighment of hepatic progenitor cells in the developing mouse liver", *Hepatol.*, 32:1230-1239 (2000).

* cited by examiner

Phenotypic analysis of human adult liver cells

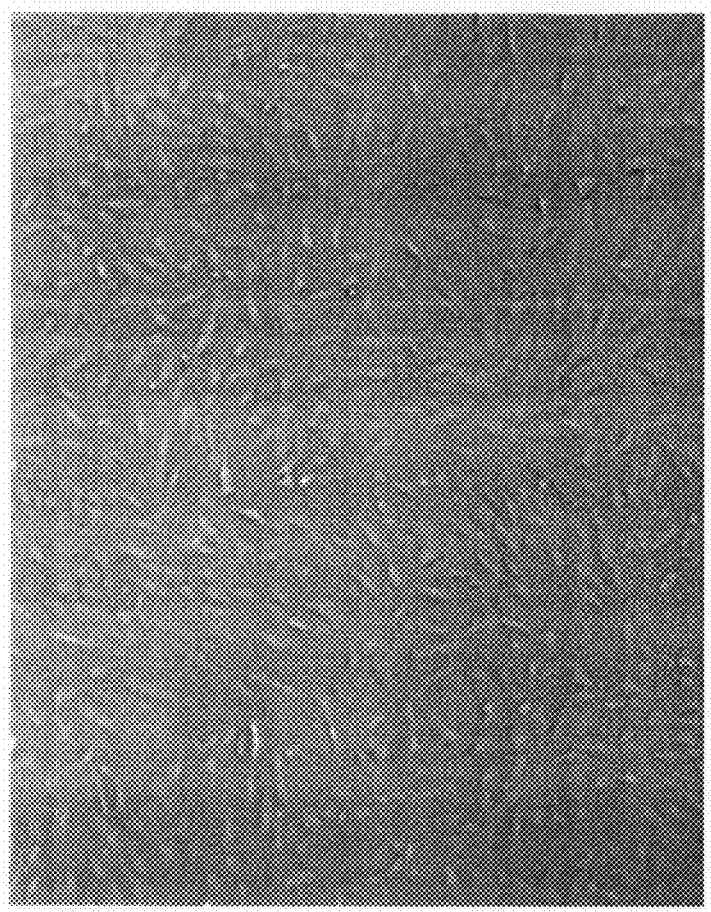
Figure 11: In vitro expansion of the liver engrafting cells on stroma free culture

Limiting Dilution Analysis of human liver engrafting cells (LEC) after Sorting

| | ALB | AAT | AFP |
|---|---|---|---|
| R1 and R2 | 1/14,975 | 1/374,377 | 0 |
| R2 | 1/308 | 1/249 | 1/940 |
| R2 5E12+ | 1/20 | 1/28 | 1/74 |
| R2 5E12- | 1/1,546 | 1/916 | 1/7,488 |
| R2 5E12+ HLA$^{low}$ | 1/7 | 1/4 | 1/59 |
| R2 5E12+ HLA+ | 1/2,135 | 1/1,053 | 1/374,378 |

FOLD DIFFERENCE IN LEC ACTIVITY

| | ALB vs. R2 | AAT vs. R2 | AFP vs. R2 |
|---|---|---|---|
| R2 | N/A | N/A | N/A |
| R2 5E12+ | 15.4 | 8.9 | 12.7 |
| R2 5E12- | -5 | -3.6 | -7.9 |
| R2 5E12+ HLA$^{low}$ | 44 | 62.2 | 15.9 |
| R2 5E12+ HLA+ | -6.9 | -4.2 | -398 |

Table 2

Screening for LEC by immunostaining (ck19+/Alb+)

| TISSUE# | SAMPLE | | COLONY FREQUENCY | FOLD DIFFERENCE | |
|---|---|---|---|---|---|
| | | | | vs Total | vs 5E12- |
| Sample A Fresh Tissue | TOTAL CELLS | | 1/1,045 | | |
| | 5E12 POST MACS | | 1/218 | 4.8 | |
| Sample B Fresh Tissue | TOTAL CELLS | | 1/1487 | | |
| | 5E12 POST MACS | | 1/291.6 | 5.1 | |
| Sample C Frozen Tissue | TOTAL CELLS | | 1/306 | | |
| | 5E12 POST MACS | | 1/57.3 | 5.3 | |
| | SORTED CELLS | R2*5E12- | 1/711 | -2.3 | |
| | | R2*5E12+ | 1/96.1 | 3.2 | 7.4 |
| | | R2*5E12+ POST MACS | 1/80.0 | 3.8 | 8.8 |
| Sample D Fresh Tissue | SORTED CELLS | R2 | 1/691 | | |
| | | R2*5E12- | 1/21413 | -30.9 | |
| | | R2*5E12+ | 1/2000.0 | -2.9 | 10.7 |

Table 3

HUMAN LIVER ENGRAFTING CELLS ISOLATED FROM ADULT LIVER TISSUE

RELATED APPLICATIONS

This application is a continuation of U.S. Ser. No. 10/177,178, filed Jun. 21, 2002, now U.S. Pat. No. 7,211,404, which issued on May 1, 2007, and which claims priority to U.S. Ser. No. 60/300,535, filed Jun. 22, 2001. Each of these applications is herein incorporated by reference in its entirety.

The body depends on the liver to perform a number of vital functions, including regulation, synthesis, and secretion of many substances important in maintaining the body's normal state; storage of important nutrients such as glycogen (glucose), vitamins, and minerals; and purification, transformation, and clearance of waste products, drugs, and toxins. However, its distinctive characteristics and activities render it susceptible to damage from a variety of sources, and such damage can have enormous impact on a person's health.

The most abundant and metabolically active cells in the liver are the hepatocytes. The lobules of the liver are hexagonal in shape, with six portal triads at the periphery, each containing a branch of the portal vein, a branch of the hepatic artery, and a bile duct, all held tightly together by a layer of hepatocytes. Hepatocytes rarely divide, but they have a unique capacity to reproduce in response to an appropriate stimulus, such as the removal of a portion of liver. This process involves controlled hyperplasia, that usually restores the liver to within 5 to 10% of its original weight.

The liver has a unique capacity to regenerate after injury. The process begins with proliferation of "mature" hepatocytes; other cell lineages including biliary epithelial cells (BEC) and sinusoidal cells proliferate somewhat later. Liver regeneration plays an important role after partial hepatectomy and after injuries that destroy portions of the liver, such as viral, toxic, or ischemic damage. However, excessive damage can reach a "point of no return", and normal tissue is then replaced with scar tissue. The liver's ability to regenerate is also compromised by pre-existing or repeated liver damage or disease.

It has been found that a number of surface determinants are shared between bone-marrow derived stem cells, and cells that can give rise to hepatocytes, including c-kit, CD34, and Thy-1 in rodents, and c-kit and CD34 in humans (see Omori et al., (1997) *Hepatology* 26: 720-727; Lemmer et al. (1998) *J. Hepatol* 29: 450-454; Peterson et al. (1998) *Hepatology* 27: 433-445; ibid (1999) *Science* 284:1168-1170; Baumann et al., (1999) *Hepatology* 30: 112-117; Lagasse et al. (2000) *Nature Med.* 11:1229-1234). These findings may have important clinical implications for gene therapy and hepatocyte transplantation, two innovative approaches to the treatment of fulminant hepatic failure and genetic metabolic disorders of the liver.

Some evidence has indicated that some immature liver cell lines can differentiate into both BEC and hepatocytes. For example, Fiorino at al. (1998) *In Vitro Cell Dev Biol Anim* 34(3):247-58 report isolation of a conditionally transformed liver progenitor cell line. Coleman and Presnell (1996) *Hepatology* 24(6):1542-6 discuss phenotypic transitions in proliferating hepatocyte cultures that suggest bipotent differentiation capacity of mature hepatocytes. Oval cell precursors are thought to be located either in the canals of Herring or next to the bile ducts. Bile duct cells are required for oval cell proliferation, indicating that either it is the source of the precursors or it acts in a supportive or inductive role. Kubota et al., International Patent Application WO02/28997 discloses an ICAM-1 expressing progenitor cell population.

Intermediate filament proteins, particularly bile duct-specific cytokeratin 19 (CK19) and the hepatocyte-specific HepPar1 antigen can help define the developmental stages of hepatic progenitor cells during liver morphogenesis. Ductular hepatocytes proliferate and share phenotypic characteristics with hepatocytes and BEC. As hepatocyte differentiation progresses, expression of HepPar1 antigen increases, and expression of CK14 and CK19 are lost. In contrast, as progenitor cells are transformed into ductal plate cells, CK19 expression increases in differentiated bile ducts, while CK14 and HepPar1 antigens are lost. Hepatic progenitor cells therefore may differentiate in steps marked by the acquisition or loss of specific phenotypic characteristics. Commitment of the progenitor cells to either hepatocyte or bile duct epithelial cell lineages results in increased expression of one marker and loss of the other marker. Early reports suggested the in vivo presence of such bipotent progenitor cells may be found in Douarin (1975) *Med. Biol.* 53:427-455; Shiojiri et al., (1991) *Cancer Res.* 51: 2611-2620; Haruna et al. (1996) *Hepatology* 23(3):476-81; Tateno and Yoshizato (1996) *Am J Pathol* 149(5):1593-605; and Haque et al. (1996) *Lab Invest* 75(5):699-705. The expression of albumin and alpha-fetoprotein are also useful markers for hepatocytes.

A discussion of hepatic progenitor cells may be found in Susick et al. (2001) *Ann. N.Y. Acad. Sci.* 944:398-419; in U.S. Pat. No. 5,576,207; and U.S. Patent Application no. 20020016000.

To achieve a further characterization of hepatic progenitor cells, and the cells derived therefrom, it is critical to have well defined model systems, that can decipher the complex interplay between "environmental" factors and intrinsic cellular factors that regulate cell renewal, as well as the phenotypic definition of the specific cells capable of giving rise to mature hepatic cells. Identification and characterization of factors regulating specification and differentiation of cell lineages in the developing and adult liver, and in the biliary tree are of great interest. The further characterization of liver engrafting cells is of great scientific and clinical interest.

SUMMARY OF THE INVENTION

Methods are provided for the separation and characterization of liver engrafting cells (LEC), which are progenitor cells having the ability to engraft the liver and give rise to differentiated hepatic cells. The cells can be separated on the basis of forward scatter and autofluorescence, and/or by expression of specific cell surface markers. The cells are useful in transplantation, for experimental evaluation, and as a source of lineage and cell specific products, including mRNA species useful in identifying genes specifically expressed in these cells, and as targets for the discovery of factors or molecules that can affect them.

In vitro and in vivo systems are provided for the growth and analysis, including clonal analysis, of liver engrafting cells. Clonogenic assays may be performed in vitro in the presence of a feeder layer of stromal cells. The cells can also be expanded in vitro in the absence of feeder layers. These culture systems are suitable for growth and characterization of liver engrafting cells. In vivo the cells engraft the liver, and engraftment may be experimentally tested by repopulation of liver, cells in FAH deficient animals.

The liver engrafting cells find use in the evaluation of therapies relating to liver specific viruses, e.g. hepatitis A, B, C, D, E viruses, etc., particularly human hepatitis viruses. The cells also find use in toxicology testing, for the production of hepatocytes in culture, and as a means of providing the by-products of liver metabolism, e.g. the products of drug transformation by liver cells.

BRIEF DESCRIPTION OF THE DRAWINGS

FIGS. 4A, 4D and 4G show a 5E12 vs. HLA class I staining. The polygonal regions illustrate the gates used to select for 5E12$^+$, HLA$^{low}$ LEC. FIGS. 4B, 4E and 4H show corresponding plots utilizing E-cadherin; EpCam and CD49f, respectively, as the x axis. FIGS. 4C, 4F and 4I show the analysis of the populations gated in FIGS. 4B, 4E and 4H, for expression of 5E12. The data demonstrate equivalence of staining between 5E12, EpCam, E-cadherin and CD49f.

FIGS. 10A-10F are serial sections from a single liver. These data demonstrate the ability of LEC to generate hepatocytes. The areas where human albumin is expressed are also positive for CK19.

FIGS. 10A to 10H show the staining of LEC in fetal and adult liver.

FIG. 11 shows the morphology of the liver engrafting cells after two weeks in culture, in which they grow as a typical epithelial cell monolayer.

Table 2 shows limiting dilution of human liver engrafting cells.

Table 3 shows screening for LEC by immunostaining.

DESCRIPTION OF THE SPECIFIC EMBODIMENTS

Liver engrafting cells (LEC) are isolated and characterized, and demonstrated to be progenitor cells capable of developing into hepatocytes when transplanted in vivo. The cell populations enriched for liver engrafting cells are useful in transplantation to provide a recipient with restoration of liver function; for drug screening; in vitro and in vivo models of hepatic development; in vitro and in vivo screening assays to define growth and differentiation factors, and to characterize genes involved in liver development and regulation; and the like. The native cells may be used for these purposes, or they may be genetically modified to provide altered capabilities.

The ability to develop into regenerating hepatocytes can be assessed in vivo, e.g. in immunodeficient animals, e.g. RAG, SCID, nude, etc., in the FAH$^{-/-}$ animals, or FAH knockout immunodeficient animals with allogeneic, syngeneic or xenogeneic donor cells, by the ability of these donor cells to provide functionality in this system. FAH expression is a defect of the human genetic disorder, tyrosinemia type 1. FAH function is provided by the engrafted hepatocytes. Alternatively, in vitro methods may be used for the assessment of biological function, by the cultivation of with appropriate growth factors and/or cytokines under hepatocyte generating conditions. When grown in culture, the subject cells grow as a monolayer, with a typical epithelial cell morphology.

Figure 1:
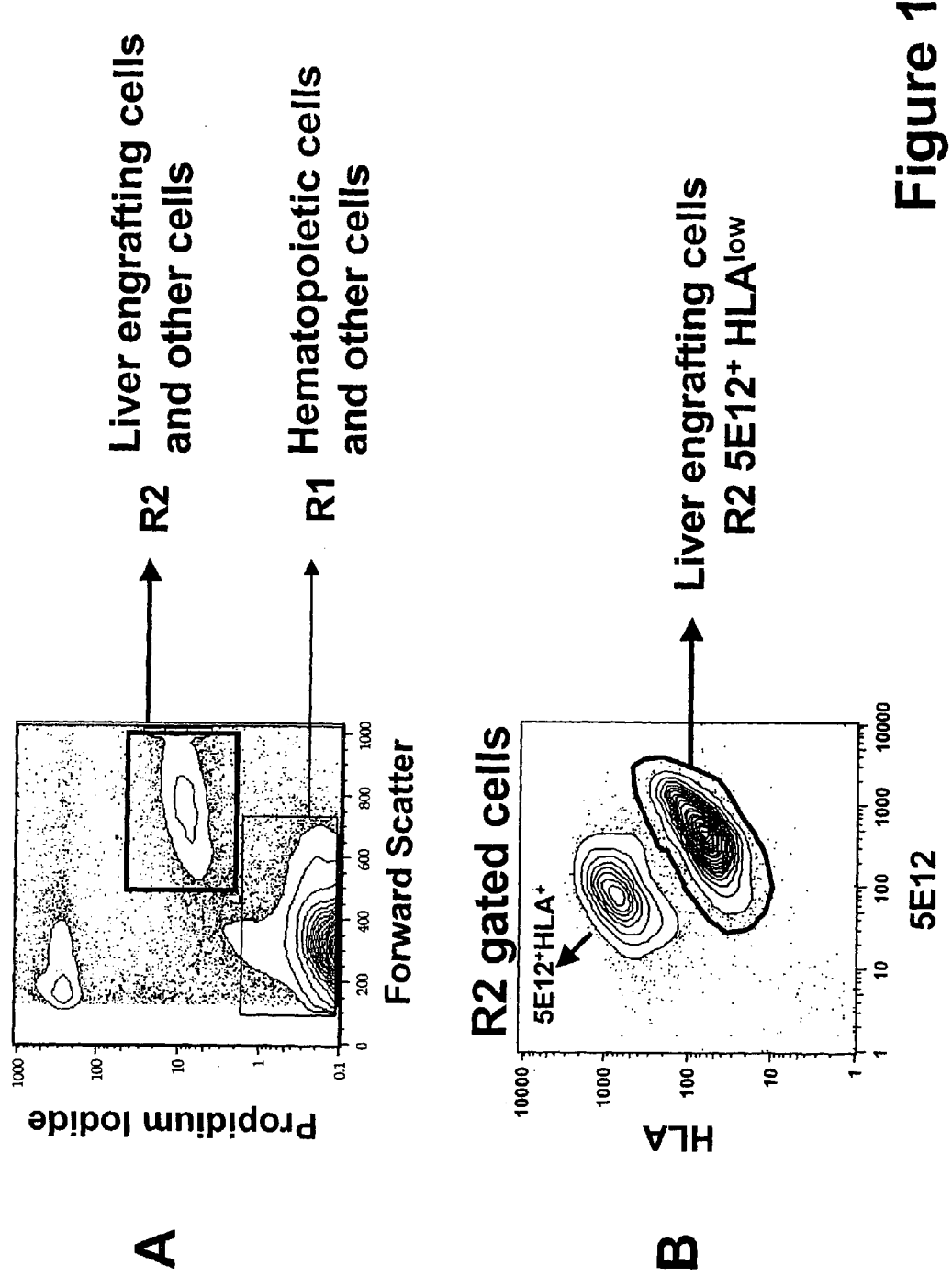
FIG. 1A shows the staining of human fetal liver cells for forward scatter, autofluorescence, and viability (propidium iodide), and separation into an R1 and R2 population on the basis of these characteristics.
FIG. 1B shows the expression of the 5E12 and HLA Class I epitopes on subpopulations of cells in the R2 population.

The liver engrafting cells of the present invention may be enriched on the basis of viability, forward scatter, autofluorescence, and expression of cell surface markers. For example, after staining with propidium iodide (PI) dead cells stain brightly because they are unable to exclude the dye. Whereas viable cells are negative to low when stained with propidium iodide. The cells of interest are found in the PI$^{low}$ subpopulation, between the very bright and the negative, as shown in FIG. 1. Forward scatter may also be used to gate for the cells of interest, which have a high forward scatter; as shown in FIG. 1.

Within the population of high forward scatter, PI$^{low}$ cells, the liver engrafting cells are positively and/or negatively selected for expression of specific markers. By flow cytometry analysis and sorting of cell surface markers, such as those described below, viable cells can be sorted. One such marker of interest for positive selection is the 5E12 epitope. Other markers, that may be used interchangeably with 5E12 for positive selection, include ep-cam, e-cadherin, and CD49f. Preferably the cells are also selected for low expression of HLA Class I antigens, i.e. HLA-A, HLA-B and HLA-C. Other markers, that may be used interchangeably with HLA Class I antigens, include CD38 and CD54. Additionally, the cells may also be negatively selected, or characterized as negative for, expression of CD117 and/or CD14. Although not usually used for selection, expression of both cytoplasmic proteins albumin and CK19 is characteristic of LEC.

DEFINITIONS

In the definitions of markers and cells provided below, the terms will typically be defined in terms of human proteins, cells, and the like, where human cells are a preferred embodiment of the invention. It will be understood by those of skill in the art that other mammals may also be used as a source of cells, and that selection of cells from such non-human species will utilize the counterpart homologous and functionally related markers for that species.

Liver engraftment. As used herein, the term "liver engrafting cells" refers to a progenitor cell population that, when transplanted into an animal, gives rise to mature hepatocytes. The developmental potential of liver progenitor cells can be assessed by functional and phenotypic criteria. Functionally, hepatocytes are characterized by their ability to complement FAH deficiency, and by the expression of liver specific proteins, including albumin, alpha-1-antitrypsin, alpha fetoprotein, etc. Hepatocytes are also functionally characterized by their ability to be infected by hepatitis viruses, e.g. Hepatitis A (HAV); Hepatitis B (HBV), hepatitis C (HCV); Hepatitis D (HDV); Hepatitis E (HEV); etc. The liver engrafting cells of the invention are also able to give rise to BEC, which can be functionally characterized by expression of cytokeratin 19, by multicellular ductal formation and the formation of biliary canaliculi between individual monolayer cells.

Positive and negative staining. The subject liver engrafting cells are characterized: by their expression of cell surface markers. While it is commonplace in the art to refer to cells as "positive" or "negative" for a particular marker, actual expression levels: are a quantitative trait. The number of molecules on the cell surface can vary by several logs, yet still be characterized as "positive". It is also understood by those of skill in the art that a cell which is negative for staining, i.e. the level of binding of a marker specific reagent is not detectably different from a control, e.g. an isotype matched control; may express minor amounts of the marker. Characterization of the level of staining permits subtle distinctions between cell populations.

The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining above the brightness of an isotype matched control, but is not as intense as the most brightly staining cells normally found in the population. Low positive cells may have unique properties that differ from the negative and brightly stained positive cells of the sample. An alternative control may utilize a substrate having a defined density of marker on its surface, for example a fabricated bead or cell line, which provides the positive control for intensity.

Sources of Progenitor Cells. Ex vivo and in vitro cell populations useful as a source of cells may include fresh or frozen liver cell populations, bile duct cell populations, or pancreatic cell populations, etc. obtained from embryonic, fetal, pediatric or adult tissue. The methods can include further enrichment or purification procedures or steps for cell isolation by positive selection for other cell specific markers. The progenitor cells may be obtained from any mammalian species, e.g. human, equine, bovine, porcine, canine, feline, rodent, e.g. mice, rats, hamster, primate, etc.

R2 population. Populations of cells comprising liver engrafting progenitor cells as described above can be separated on the basis of forward scatter, autofluorescence, and viability in the presence of a vital dye (such as propidium iodide, 7-AAD, etc). The R2 population, as used herein, refers to a population of live, high forward scatter, autofluorescent cells, as shown in FIG. 1. After staining with the vital dye propidium iodide (PI) the cells of interest do not stain brightly, i.e. they are ($PI^{low}$). This population of cells is enriched for liver engrafting progenitor cells and also contains some contaminating cells, which may be fibroblasts, endothelial cells, and the like.

5E12. The liver engrafting cells of the invention are positive for expression of 5E12 antigen. The 5E12 monoclonal antibody was originally raised against human neural cells. The antibody recognizes a protein of approximately 125 kDa. The hybridoma cell line producing the 5E12 monoclonal antibody has been deposited with the American Type Culture Collection, accession number PTA-994, on Dec. 20, 1999.

Ep-cam. The liver engrafting cells of the invention are positive for expression of ep-cam. This antigen is also known as epithelial surface antigen (ESA) and epithelial glycoprotein 2 (EGP-2). Ep-cam mediates $Ca^{2+}$-independent homotypic cell-cell adhesions. In vivo expression of Ep-CAM is related to increased epithelial proliferation and negatively correlates with cell differentiation. A regulatory function of Ep-CAM in the morphogenesis of epithelial tissue has been demonstrated for a number of tissues. The sequence is disclosed by Szala et al. (1990) *Proc. Nat. Acad. Sci.* 87:3542-3546. Antibodies are commercially available, for example from BD Biosciences, Pharmingen, San Diego, Calif., catalog number 347197.

E-cadherin. The liver engrafting cells of the invention are positive for expression of e-cadherin. E-Cadherin is a 120 kDa transmembrane glycoprotein that is localized in the adherens junctions of epithelial cells. It confers calcium-dependent cell-cell adhesion through five extracellular calcium-binding repeats. Expression on the cell surface leads to cell sorting, homophilic interaction specificity being conferred by the specific extracellular regions. The intracellular regions links it with the cytoplasmic partners β-catenin or plakoglobin (PG) and consequently to α-catenin and the actin filament network. Antibodies are commercially available, for example from BD Biosciences, Pharmingen, San Diego, Calif., catalog number 610181.

CD49f. The liver engrafting cells of the invention are positive for expression of CD49f. Integrin alpha-6 (CD49f) is a 150 kDa transmembrane protein, which is part of an integrin heterodimer expressed predominantly by epithelial cells. Alpha 6 associates with integrin β1 chain to form VLA-6 and with integrin (β4 chain to form the laminin and kalinin receptors. CD49f is expressed mainly on T cells, monocytes, platelets, epithelial and endothelial cells, perineural cells and trophoblasts of placenta. Its sequence may be found in Tamura et al. (1990) *J. Cell Biol.* 111:1593-1604. Antibodies are commercially available, for example from BD Biosciences, Pharmingen, San Diego, Calif., catalog number 557511.

HLA Class I. The liver engrafting cells of the invention are negative to low for class I HLA expression. Examples of class I loci are HLA-A, -B, and -C. The class I MHC antigens are polymorphic 2-chain cell surface glycoproteins. The light chain of class I antigens is beta-2-microglobulin. The heavy chain has a molecular weight of 44,000 and is made up of 3 N-terminal extracellular domains of 90 amino acids each, a small hydrophobic membrane-spanning segment and a small hydrophilic intracellular C-terminal domain, see Malissen et al. (1982) *Proc. Nat. Acad. Sci.* 79: 893-897. Antibodies are commercially available, for example from BD Biosciences, Pharmingen, San Diego, Calif., catalog number 557349, which reacts with the human form of a monomorphic epitope of major histocompatibility class I antigens.

CD 54. The liver engrafting cells of the invention isolated from adult liver tissue are negative for expression of CD54. Cells isolated from fetal tissue may be negative or positive for expression of CD54, but are generally less bright than CD54 positive cells, e.g. cells found in the $5E12^-$-population. CD54 is also known as intercellular adhesion molecule (ICAM-1), 90 (kDa). The CD54 antigen is a ligand for the leucocyte function-associated antigen-1 (CD11 a/CD18) and influences both LFA-1-dependent adhesion of leucocytes to endothelial cells and immune functions involving cell-to-cell contact. The CD54 antigen can be inducible on fibroblasts, epithelial cells, and endothelial cells. In normal tissue, CD54 antigen density is highest in endothelium and is increased by factors such as exposure to cytokines, inflammation, and neoplastic transformation. The nucleotide sequence of ICAM-1 is disclosed by Simmons et al. (1988) *Nature* 331:624-627, 1988. Antibodies are commercially available, for example from BD Biosciences, Pharmingen, San Diego, Calif., Cat. No. 347977.

CD117. The liver engrafting cells of the invention are negative for expression of CD117. CD117 recognizes the receptor tyrosine kinase c-Kit. This receptor has been particularly implicated with stem cells, including hematopoietic stem cells. Multiple isoforms of c-Kit also exist as a result of alternate mRNA splicing, proteolytic cleavage and the use of cryptic internal promoters in certain cell types. Structurally, c-Kit contains five immunoglobulin-like domains extracellularly and a catalytic domain divided into two regions by a 77 amino acid insert intracellularly; the sequence may be found in Yarden et. al. (1987) *EMBO J.* 6 (11):3341-3351. Antibodies are commercially available, for example from BD Biosciences, Pharmingen, San Diego, Calif., Cat. No. 340529.

CD14. The liver engrafting cells of the invention are negative for expression of CD14. CD14 is a single-copy gene encoding 2 protein forms: a 50- to 55-kD glycosylphosphatidylinositol-anchored membrane protein (mCD14) and a monocyte or liver-derived soluble serum protein (sCD14) that lacks the anchor. Both molecules are critical for lipopolysaccharide (LPS)-dependent signal transduction, and sCD14 confers LPS sensitivity to cells lacking mCD14. The sequence may be found in Govert et al. (1988) *Science* 239: 497-500. Antibodies are commercially available, for example from BD Biosciences, Pharmingen, San Diego, Calif.

CD34. The liver engrafting cells of the invention may be negative or positive for CD34 expression. CD34 is a monomeric cell surface antigen with a molecular mass of approximately 110 kD that is selectively expressed on human hematopoietic progenitor cells. The gene is expressed by small vessel endothelial cells in addition to hematopoietic progenitor cells and is a single-chain 105-120 kDa heavily O-glycosylated transmembrane glycoprotein. The sequence is disclosed by Simmons et al. (1992) *J. Immun.* 148:267-271. Antibodies are commercially available, for example from BD Biosciences, Pharmingen, San Diego, Calif., catalog number 550760.

CD38. The liver engrafting cells of the invention may be negative or positive for expression of CD38, but are generally less bright than CD38 positive cells, e.g. cells found in the 5E12⁻population. CD38 is a 300-amino acid type II transmembrane protein with a short N-terminal cytoplasmic tail and 4 C-terminal extracellular N-glycosylation sites. The sequence is disclosed by Jackson et al. (1990) *J. Immun.* 144: 2811-2815. The marker is generally associated with lymphocytes, myeloblasts, and erythroblasts. Antibodies are commercially available, for example from BD Biosciences, Pharmingen, San Diego, Calif., catalog number 347680.

Isolation of Liver Engrafting Cells

The subject liver engrafting cells are separated from a complex mixture of cells by techniques that enrich for cells having the characteristics as described. For example, a population of cells may be selected from the R2 population, for expression of one or more of 5E12, e-cadherin, ep-cam and CD49f. The cells are optionally selected for low or negative expression of HLA Class I antigens (herein termed HLA$^{low}$) CD54 and CD38 may be used interchangeably with HLA.

For isolation of cells from tissue, an appropriate solution may be used for dispersion or suspension. Such solution will generally be a balanced salt solution, e.g. normal saline, PBS, Hanks balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The subject cells are large, blast cells, therefore an initial separation may select for large cells by various methods known in the art, including elutriation, Ficoll-Hypaque or flow cytometry using the parameters of forward and obtuse scatter to gate for blast cells Separation of the subject cell population will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, 7-AAD). Any technique may be employed which is not unduly detrimental to the viability of the selected cells.

The affinity reagents may be specific receptors or ligands for the cell surface molecules indicated above. The details of the preparation of antibodies and their suitability for use as specific binding members are well known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium which maintains the viability of the cells. A preferred medium is phosphate buffered saline containing from 0.1 to 0.5% BSA. Various media are commercially available and may be used according to the nature of the cells, including Dulbeccos Modified Eagle Medium (dMEM), Hank's Basic Salt Solution (HBSS), Dulbeccos phosphate buffered saline (dPBS), RPMI, Iscoves medium, PBS with 5 mM EDTA, etc., frequently supplemented with fetal calf serum, BSA, HSA, etc.

The labeled cells are then separated as to the phenotype described above. The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscoves medium, etc., frequently supplemented with fetal calf serum.

Compositions highly enriched for liver engrafting activity are achieved in this manner. The subject population will be at or about 50% or more of the cell composition, and usually at or about 90% or more of the cell composition, and may be as much as about 95% or more of the live cell population. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded by use of growth factors and/or stromal cells for proliferation and differentiation.

The present methods are useful in the development of an in vitro or in vivo model for hepatocyte functions and are also useful in experimentation on gene therapy and for artificial organ construction. The developing hepatocytes serve as a valuable source of novel growth factors and pharmaceuticals and for the production of viruses or vaccines (e.g., hepatitis viruses), as well as for the study of liver parasites or of parasites having a stage of development in the liver, e.g. malarial organisms), for in vitro toxicity and metabolism testing of drugs and industrial compounds, for gene therapy experimentation (since the liver is the largest vascular organ of the body), for the construction of artificial transplantable livers, and for liver mutagenesis and carcinogenesis studies.

Functional Assays

An assay of interest for determining the in vivo capability of hepatic progenitor cells is an animal model of hereditary tyrosinemia type 1, a severe autosomal recessive metabolic disease which affects the liver and kidneys and which is caused by deficiency of the enzyme fumarylacetoacetate hydrolase (FAH). Treatment of mice homozygous for the FAH gene disruption (FAH$^{-/-}$) with 2-(2-nitro-4-trifluoromethylbenzyol)-1,3-cyclohexanedione (NTBC) abolishes neonatal lethality and corrects liver and kidneys functions. The animal model is described, for example, by Grompe et al. (1995) *Nature Genetics* 10:453-460; Overturf et al. (1996) *Nat. Genet.* 12(3):266-73; etc.

In one embodiment of the invention, an FAH mouse is reconstituted with liver engrafting cells, which may be human progenitor cells, or mouse cells comprising a detectable marker. For example, the cells may be introduced into the mouse, which may be an irradiated mouse, and allowed to first reconstitute the liver, then NTBC is withdrawn in order to select for hepatic reconstitution. Alternatively, NTBC may be withdrawn immediately after introduction of the liver engrafting cells. The reconstituted animals are useful for screening vaccines and antiviral agents against hepatic viruses, e.g. Hepatitis A, B, C, D, E; metabolic and toxicity testing of biologically active agents; and the like.

In Vitro Cell Culture

The enriched cell population may be grown in vitro under various culture conditions. When grown in culture; the subject cells grow as a monolayer, with a typical epithelial cell morphology. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The subject cells may be grown in a co-culture with feeder layer cells. Stromal cells suitable for use as feeder layers include bone marrow stromal cells, e.g. the SYS-1 cell line, FFS-1 fibroblast cell line, etc. Other cells that can be used as a feeder layer include fibroblasts derived from human or other animal sources; fetal fibroblasts derived by primary culture from the same species as the liver; the STO fibroblast cell line; etc. These cell layers provide non-defined components to the medium and may restrain the differentiation of the pluripotent cells. Culture in the presence of feeder layers is particularly useful for clonal culture, i.e. where a single progenitor cell is expanded to a population.

Functional assays may be performed using in vitro cultured cells, particularly clonogenic cultures of cells. For example, cultured cells may be assessed for their ability to express liver specific proteins, including albumin and alpha-1 antitrypsin. Expression may utilize any convenient format, including RT-PCR, ELISA for presence of the protein in culture superannuates, etc. Cultured cells may also be assessed for their ability to express bile duct proteins, e.g. CK19.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Specific growth factors that may be used in culturing the subject cells include but are not limited to hepatocyte growth factor/scatter factor (HGF), EGF, TGFα, acidic FGF (see Block et al; J. Biol Chem, 1996 132:1133-1149). The specific culture conditions are chosen to achieve a particular purpose, i.e. maintenance of progenitor cell activity, etc. In addition to, or instead of growth factors, the subject cells may be grown in a co-culture with stromal or feeder layer cells. Feeder layer cells suitable for use in the growth of progenitor cells are known in the art.

The subject co-cultured cells may be used in a variety of ways. For example, the nutrient medium, which is a conditioned medium, may be isolated at various stages and the components analyzed. Separation can be achieved with HPLC, reversed-phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions that promote progenitor cell activity.

The subject cells can be expanded in culture in a stromal cell-free medium, e.g. as described by Suzuki et al. (2000) *Hepatology* 32:1230-1239. Such cultures preferably are grown on a substrate giving a coating of extracellular matrix components(s), e.g. laminin, Type IV collagen, Type I collagen, fibronectin, etc. The medium generally comprises growth factors, e.g. HGF, EGF, etc.

The liver engrafting cells may be used in conjunction with a culture system in the isolation and evaluation of factors associated with the differentiation and maturation of hepatocytes and BEC. Thus, the cells may be used in assays to determine the activity of media, such as conditioned media, evaluate fluids for growth factor activity, involvement with formation of specific structures, or the like. Cultures may also be used as a means of processing drugs and other compounds, to determine the effect of liver metabolism on an agent of interest. For example, the product of liver metabolism may be isolated and tested for toxicity and efficacy.

Transplantation

Hepatic failure involves the systemic complications associated with severe liver injury and dysfunction. It may occur in a patient without pre-existing liver disease or may be superimposed on chronic liver injury. The diagnosis of acute liver failure requires the presence of symptoms, including jaundice and encephalopathy. Fulminant hepatic failure impairs all liver functions, causing decreased bilirubin metabolism, decreased clearance of ammonia and gut-derived proteins, and decreased clotting factor production. It may also cause kidney failure, shock, and sepsis. Without a liver transplant, more than 50% of patients will die, usually from a combination of the above conditions. Mortality exceeds 50%, even in the best circumstances. Management involves general supportive measures until the liver can regenerate and resume function. In acute liver failure without pre-existing disease, liver transplant can be life-saving.

The subject cells may be used for reconstitution of liver function in a recipient. Allogeneic cells may be used for progenitor cell isolation and subsequent transplantation. Most of the clinical manifestations of liver dysfunction arise from cell damage and impairment of the normal liver capacities. For example, viral hepatitis causes damage and death of hepatocytes. In this case, manifestations may include increased bleeding, jaundice, and increased levels of circulating hepatocyte enzymes. Where the liver dysfunction arises from conditions such as tumors, the subject cells can be isolated from the autologous liver tissue, and used to regenerate liver function after treatment.

Liver disease has numerous causes, ranging from microbial infections and neoplasms (tumors) to metabolic and circulatory problems. Hepatitis involves inflammation and damage to the hepatocytes. This type of insult may result from infectious agents, toxins, or immunologic attack. However, the most common cause of hepatitis is viral infection. Three major viruses cause hepatitis in the United States: hepatitis viruses A, B, and C. Together, they infect nearly 500,000 people in the United States every year. In addition, bacteria, fungi, and protozoa can infect the liver, and the liver is almost inevitably involved to some extent in all blood-borne infections.

Numerous medications can damage the liver, ranging from mild, asymptomatic alteration in liver chemistries to hepatic failure and death. Liver toxicity may or may not be dose-related. Tylenol (Acetominophen) is an hepatotoxic drug; Dilantin (an anti-convulsant) and isoniazid (an anti-tuberculosis agent) are examples of drugs that can cause "viral-like" hepatitis. Both environmental and industrial toxins can cause a wide variety of changes in the liver. Hepatic damage is not necessarily dose-dependent and can range from mild, asymptomatic inflammation to fulminant failure or progressive fibrosis and cirrhosis.

Problems with metabolic processes in the liver can be either congenital or acquired. Some of these disorders, such as Wilson's disease and hemochromatosis, can present as hepatitis or cirrhosis. Wilson's disease is a rare inherited condition characterized by an inability to excrete copper into bile, resulting in the toxic accumulation of copper in the liver and nervous system. Hemochromatosis is an iron overload syndrome causing iron deposits and consequent damage to various organs, including the liver, heart, pancreas, and pituitary gland. The disease may be due to an inherited increase in gut absorption of iron or to multiple blood transfusions, since iron is normally found in circulating red blood cells.

The liver may be affected by numerous conditions, particularly autoimmune disorders, in which the immune system attacks the body's own normal tissues. Some examples include rheumatic diseases, such as systemic lupus erythematosus and rheumatoid arthritis, and inflammatory bowel diseases, such as ulcerative colitis and Crohn's disease.

Genes may be introduced into the cells prior to culture or transplantation for a variety of purposes e.g. prevent or reduce susceptibility to infection, replace genes having a loss of function mutation, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to transfect the target cells, e.g. electroporation, calcium precipitated DNA, fusion, transfection, lipofection and the like. The particular manner in which the DNA is introduced is not critical to the practice of the invention.

Many vectors useful for transferring exogenous genes into mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. For examples of progenitor and stem cell genetic alteration, see Svendsen et al. (1999) *Trends Neurosci.* 22(8): 357-64; Krawetz et al. (1999) *Gene* 234(1):1-9; Pellegrini et al. *Med Biol Eng Comput.* 36(6):778-90; and Alison (1998) *Curr Opin Cell Biol.* 10(6):710-5.

Alternatively, the liver progenitors can be immortalized-disimmortalized (for example, see Kobayashi et al. (2000) *Science* 287:1258-1262. In such a procedure, an immortalizing genetic sequence, e.g. an oncogene, is introduced into the cell, in such a manner that it can be readily removed, for example with a site specific recombinase such as the cre-lox system.

To prove that one has genetically modified progenitor cells, various techniques may be employed. The genome of the cells may be digested with restriction enzymes and used with or without DNA amplification. The polymerase chain reaction; gel electrophoresis; restriction analysis; Southern, Northern, and Western blots; sequencing; or the like, may all be employed. The cells may be grown under various conditions to ensure that the cells are capable of differentiation while maintaining the ability to express the introduced DNA. Various tests in vitro and in vivo may be employed to ensure that the pluripotent capability of the cells has been maintained.

The cells may be administered in any physiologically acceptable medium, normally intravascularly, including intravenous, e.g. through the hepatic portal vein; intrasplenic, etc. although they may also be introduced into other convenient sites, where the cells may find an appropriate site for regeneration and differentiation. Usually, at least $1\times10^3$/Kg cells will be administered, more usually at least about $1\times10^4$/Kg, preferably $1\times10^6$/Kg or more. The cells maybe introduced by injection, catheter, or the like The subject cells find use in as cultured cells, and for the generation of hepatocytes for bioartificial liver bioreactors, in which the hepatocytes are separated by a membrane or other physical barrier from the perfusate stream. Four devices (Circe Biomedical HepatAssist®, Vitagen ELAD™, Gerlach BELS, and Excorp Medical BLSS) that utilize hepatocytes cultured in hollow-fiber membrane are currently in clinical evaluation. While the development of bioartificial liver assist devices (BLADs) for the treatment of acute liver failure, either fulminant or acute decompensation on chronic liver failure, is of great interest, it has been difficult to accomplish, in part because hepatocytes are extremely difficult to maintain in culture. By culturing the subject liver engrafting cells, a constant supply of hepatocytes is provided for such devices.

Bioartificial liver bioreactors provides one or more of the functions: oxidative detoxification (primarily through the cytochrome P450 enzyme system); biotransformation (e.g., urea synthesis, gluconuridation, and sulfation); excretion (through the bile system); protein and macromolecule synthesis; intermediate metabolism (gluconeogenesis, fatty acid, and amino acid); and immune and hormonal system modulation.

Current BLADs in clinical evaluation are based on the use of hollow-fiber cartridges housing hepatocytes cultured in the extraluminal space of the hollow fibers. Perfused through the luminal space of the hollow fiber cartridge are whole blood, or a plasma stream. An oxygenator may be placed before the bioreactors to raise the available oxygen levels in the perfusing stream, and columns or filters used to reduce toxins prior to reaching the hepatocytes.

Other devices may perfuse plasma in an axial flow path over and/or through a nonwoven polyester fabric; through channels cored in an highly porous polyurethane foam structure seeded with hepatocytes; through microporous polysulfone hollow-fiber membranes; microporous polyvinyl formal resin material; and the like. The progenitor cells, and or progeny hepatocytes may be encapsulated.

Expression Assays

Of particular interest is the examination of gene expression in liver engrafting cells. The expressed set of genes may be compared with a variety of cells of interest, e.g. adult hepatic progenitor cells, stem cells, hematopoietic cells, etc., as known in the art. For example, one could perform experiments to determine the genes that are regulated during development.

Any suitable qualitative or quantitative methods known in the art for detecting specific mRNAs can be used. mRNA can be detected by, for example, hybridization to a microarray, in situ hybridization in tissue sections, by reverse transcriptase-PCR; or in Northern, blots containing-poly $A^+$ mRNA. One of skill in the art can readily use these methods to determine differences in the size or amount of mRNA transcripts between two samples. For example, the level of particular mRNAs in progenitor cells is compared with the expression of the mRNAs in a reference sample, e.g. hepatocytes, or other differentiated cells.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., *Science* (1995) 270:484). SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific polynucleotide sequences (or restriction enzyme sites) are used as unique identifiers of genes, coupled with information about fragment length or fragment location within the expressed gene. The relative representation of an expressed gene with in a sample can then be estimated based on the relative representation of the fragment associated with that gene within the pool of all possible fragments. Methods and compositions for carrying out DD are well known in the art, see, e.g., U.S. Pat. Nos. 5,776,683; and 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Hybridization to arrays may be performed, where the arrays can be produced according to any suitable methods known in the art. For example, methods of producing large arrays of oligonucleotides are described in U.S. Pat. Nos. 5,134,854, and 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with an arrays are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., *Genome Res.* (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

In another screening method, the test sample is assayed at the protein level. Diagnosis can be accomplished using any of a number of methods to determine the absence or presence or altered amounts of a differentially expressed polypeptide in the test sample. For example, detection can utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.). The absence or presence of antibody binding can be determined by various methods, including flow cytometry of dissociated cells, microscopy, radiography, scintillation counting, etc. Any suitable alternative methods of qualitative or quantitative detection of levels or amounts of differentially expressed polypeptide can be used, for example ELISA, western blot, immunoprecipitation, radioimmunoassay, etc.

Screening Assays

The subject cells are useful for in vitro assays and screening to detect agents that affect liver engrafting cells and hepatocytes generated from the liver engrafting cells. A wide variety of assays may be used for this purpose, including toxicology testing, immunoassays for protein binding; determination of cell growth, differentiation and functional activity; production of hormones; and the like.

In screening assays for biologically active agents, viruses, etc. the subject cells, usually a culture comprising the subject cells, is contacted with the agent of interest, and the effect of the agent assessed by monitoring output parameters, such as expression of markers, cell viability, and the like. The cells may be freshly isolated, cultured, genetically altered as described above, or the like. The cells may be environmentally induced variants of clonal cultures: e.g. split into independent cultures and grown under distinct conditions, for example with or without virus; in the presence or absence of other cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing, to test the effect of hepatic viruses, e.g. Hepatitis A, B, C, D, E viruses; antiviral agents; and the like.

In addition to complex biological agents, such as viruses, candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists; etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 µl to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol.* 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1):112-225; Kawamoto et al. (1999) *Genome Res* 9(12):1305-12; and Chen et al. (1998) *Genomics* 51(3):313-24, for examples.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

EXAMPLE 1

Flow Cytometric Sorting of Human Liver Cells

Dual laser flow cytometric analyses and sorting of human liver cells from fetal and adult tissue were performed on a Becton Dickinson FACSVantage SE. An Argon Ion laser and a Helium Neon laser were utilized as the primary and secondary excitation sources emitting 150 mW at the 488 nm wavelength and 30 mW of 633 nm wavelength, respectively. Light scattered at forward and orthogonal angles was amplified linearly and measured through 48 nm bandpass filters, employing a 0.6 OD neutral density filter in front of the forward scatter detector in order to attenuate high level forward angle scatter signals resulting from populations of larger sized cells. In this configuration there is sufficient dynamic range on the forward scatter axis to capture and scale forward angle scatter signals, resulting from the diverse range of cell sizes found in liver tissue, within a single linear decade. Typical forward scatter amplifier gain settings range from 8 to 16. FITC, PE, and PI fluorochromes were all excited at 488 nm and fluorescence emissions were measured using 530/30, 585/42, 610/20 nm bandpass filters, respectively. APC and APC-Cy7 fluorochromes were excited at 633 nm and fluorescence emissions were measured using 660/20 bandpass and 750 longpass filters, respectively. All immunofluorescence measurements were amplified logarithmically.

The voltage settings for each fluorescent channel are calibrated using the Spherotech RFP 30-5 reference particle. Following calibration, compensation settings are derived empirically using single color controls.

Configuration of the fluidics setup on the flow cytometer is optimized for the unique size distribution and characteristics of cells found in liver derived tissue. A custom fabricated nozzle tip with an orifice diameter of 130 µm and a sheath pressure setting of 10 psi are used. The temperature of the sheath reservoir, the sample holder, and the receipt tube holder are all maintained at 4° C. by a refrigerated recirculator.

Clustered subpopulations of liver derived cells can be identified by adding PI to the cell suspension, subjecting the cells to flow cytometry, and analyzing the data as a plot of forward scatter versus PI fluorescence. Three distinct populations can be resolved according to the following attributes; a small cell cluster displaying low forward scatter, low level fluorescence (R1); a large cell cluster displaying high forward scatter and mid-scale fluorescence (R2), and dead cells comprising the third distinct cluster with a continuum of low to mid level forward scatter signal and very high level fluorescence. Results are shown in FIG. 1. The R2 subpopulation is demonstrated to be autofluorescent by performing the analysis described above in the absence of PI. Two distinct populations can be resolved according to the following attributes; a small cell cluster displaying low forward scatter, low level fluorescence and a large cell cluster displaying high forward scatter and mid-scale fluorescence.

Aggregates are discriminated, using pulse processing, by plotting forward scatter peak height against width, which forms the basis of the third region. A sort gate is defined as the intersection of these three regions. Primary enrichment of the target population is achieved in the first round of sorting. The enriched product may then be re-sorted to relative purity. Product purity is always verified by re-analysis.

EXAMPLE 2

Isolation of a Liver Progenitor Cell

Figure 2:
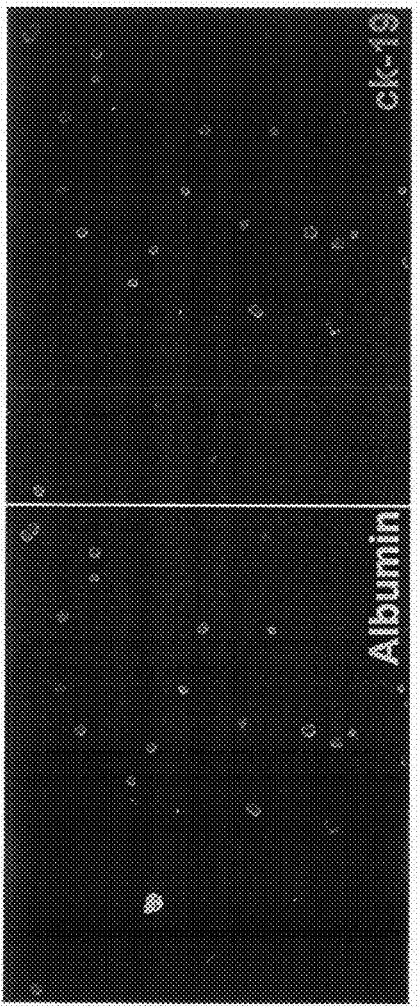
FIGS. 2A and 2B show that the R2 population is heterogeneous for expression of albumin and CK19, prior to sorting for 5E12 expression.
Figure 2:
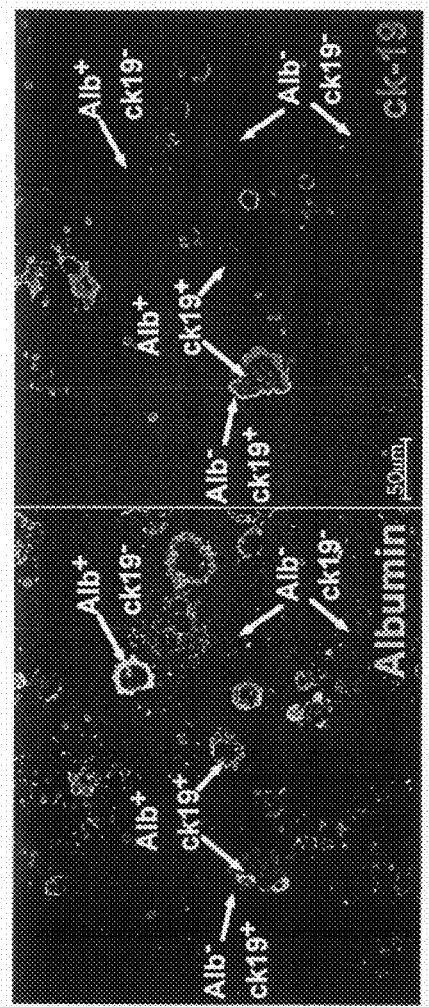

Liver cells previously frozen or freshly isolated liver cells were stained with 5E12. The cells were enriched for 5E12 by MACS column using a 5E12 Ab, then 5E12+ cells were sorted. Alternatively, 5E12+ cells were sorted directly after staining. For the sorting; cells are separated between R1 and R2 gates. R2/5E12$^+$ cells represents the majority of liver engrafting cells in an in vitro or in vivo assay. The cells were characterized by expression of ck19 and albumin in the same cell (shown in FIGS. 2A and 2B). In addition to 5E12, selection for lower levels of HLA-Class I expression enriched for liver engraftment, using antibody reactive with human HLA-Class I A,B,C (W6-32 antibody). When gating on the R2 cells, three distinct clustered subpopulations of cells can be resolved by analysis of 5E12 fluorescence versus HLA-Class I fluorescence as two-dimensional density or contour plots (FIG. 1). One subpopulation displays negative staining for both 5E12 and HLA-Class I (5E12$^-$HLA$^-$); a second subpopulation displays a lower relative level of 5E12 fluorescence and higher levels of HLA-Class I fluorescence (5E12$^-$HLA$^+$); and a third subpopulation displays higher level 5E12 fluorescence and lower level HLA-Class I fluorescence (5E12$^+$HLA$^{low}$).

While an analysis of a single stain, i.e. one color, does not necessarily provide a clear population distinction, it is clear from the Figures that in a two color plot the cells fall into distinct subpopulations.

Results

A method is provided to enrich for liver progenitor colonies by sorting for expression of cell surface antigens. From the results of a clonogenic assay of sorted human fetal liver cells: cells were sorted by viability (PI), size (FS), and autofluorescence and were then further separated by surface antibodies, and plated on FFS- or BMS-6. The proliferative capacity of the hepatic colonies generated after sorting (ck19/albumin or ck19 only) were compared after 2 weeks in culture. Only R2 gated cells (FS$^+$PI$^{low}$) generated colonies.

The 5E12 antibody enriches for human fetal and adult liver progenitor cells. FIG. 1 illustrates the staining of human fetal liver cells (16 g.w.) with 5E12 monoclonal antibodies. Cells included in the R2 gate were stained with 5E12 or isotype matched control mAb.

Table 1 and Table 2 show the results of a limiting dilution analysis of sorted 5E12 liver cells. Human fetal liver cells were enriched for 5E12 positive cells using MACS columns. L R2, 5E12 positive cells were sorted in 96 well plates on BMS-6 stroma from 1 to 500 cells per well. Human albumin expression was monitored by ELISA, in order to detect colonies of progenitor cells in the culture wells.

TABLE 1

Limiting dilution analysis of sorted 5E12 positive cells.
The analysis was done using ACDU sorted 5E12+ liver cells
and 8 dilutions points (1, 5, 10, 25, 50, 125, 250, 500 cells).
Albumin positive wells were detected by ELISA
at day 7, day 14, day 21 and day 28.

| Day | R2/5E12 |
| --- | --- |
| D7  | 1/39  |
| D14 | 1/50  |
| D21 | 1/79  |
| D28 | 1/147 |

EXAMPLE 3

Characterization of Liver Engrafting Cell Phenotype

Figure 3:
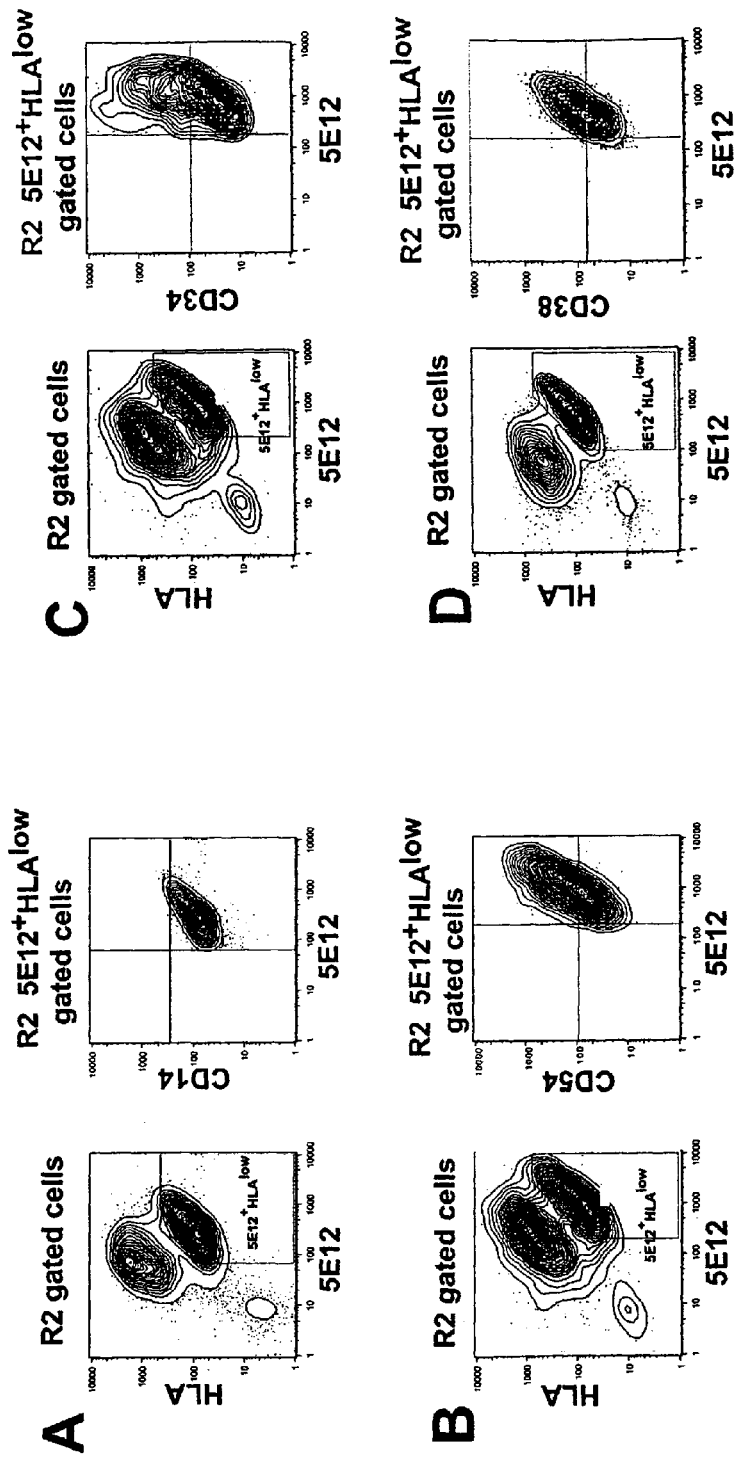
FIGS. 3A to 3D shows phenotypic analysis of human fetal liver cells.
Figure 4:
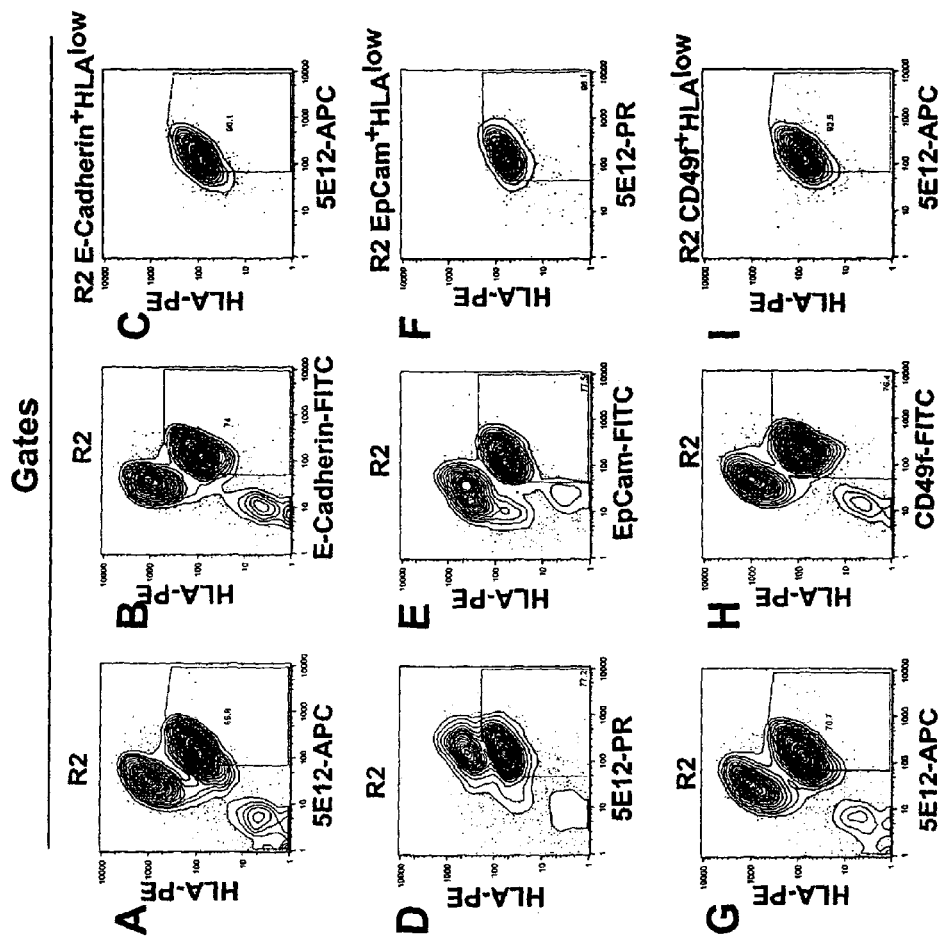
FIG. 4 shows the staining of cells from the R2 population with 5E12, EpCAM, CD49f, E-Cadherin, and HLA.
Figure 5:
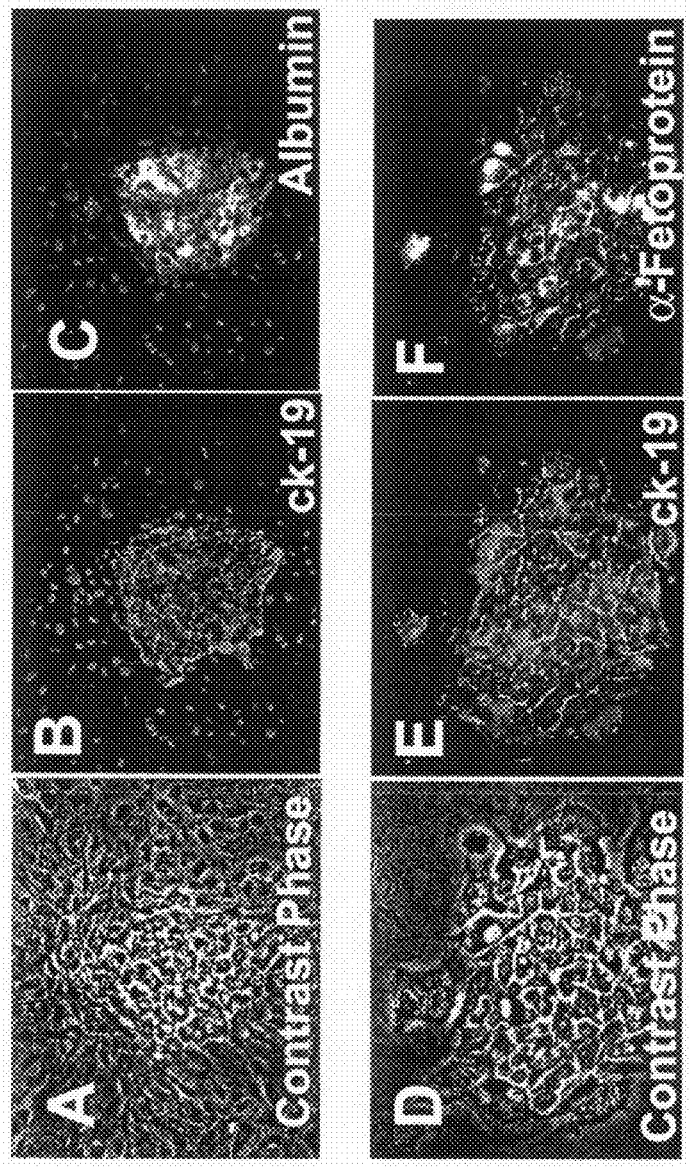
FIGS. 5A-5F show staining for albumin (alb), alpha-fetoprotein (afp) and CK19 on colonies derived from human fetal liver LEC after two weeks in culture in vitro.

Human fetal liver cells and human adult liver cells were obtained maintained at 4° C. To make a cell suspension the tissue was minced, resuspended in Ca++ free buffered saline, and digested with collagenase in the presence of hyaluronidase for 30 min at 37° C. Optionally the cell suspensions were additionally digested with trypsin/EDTA for 20 min at 37° C. The cell suspension was filtered through 70 μm nylon filter and resuspended in IMDM containing 2% FBS, 2 mM EDTA. To an aliquot of cells was added a combination of two or more antibodies, previously titrated, as shown in FIGS. 3 and 4. Isotype matched controls were utilized for all stainings. The cells were analyzed by flow cytometry as described in Examples 1 and 2.

Figure 9:
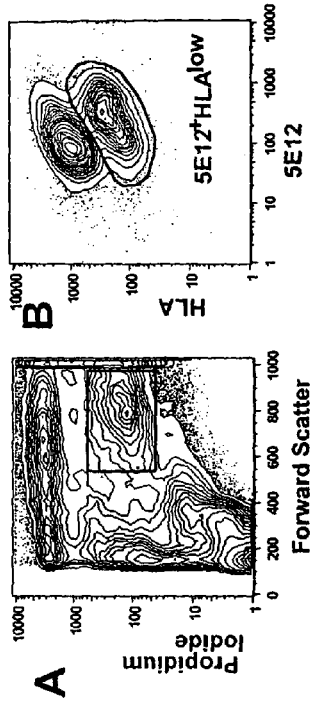
FIGS. 9A-9H show analysis of human adult liver tissue, as described for fetal cells in FIG. 3.
Figure 9:
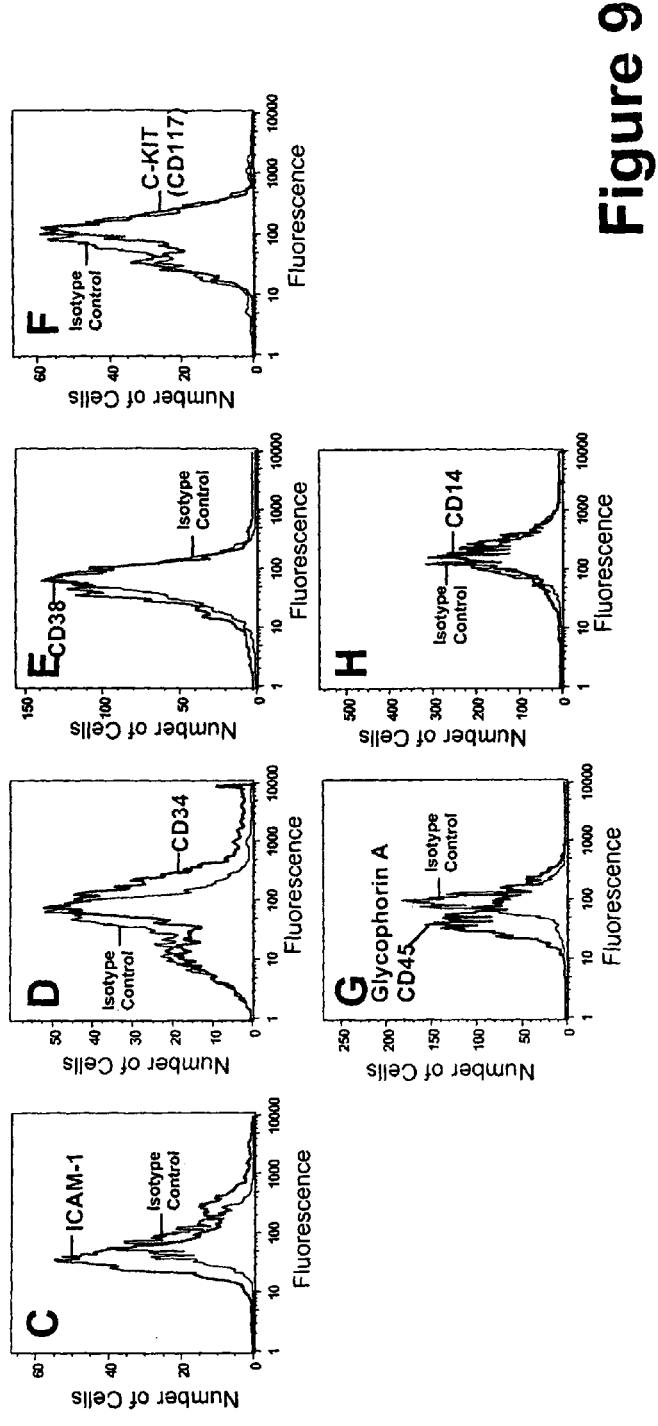
Figure 10:
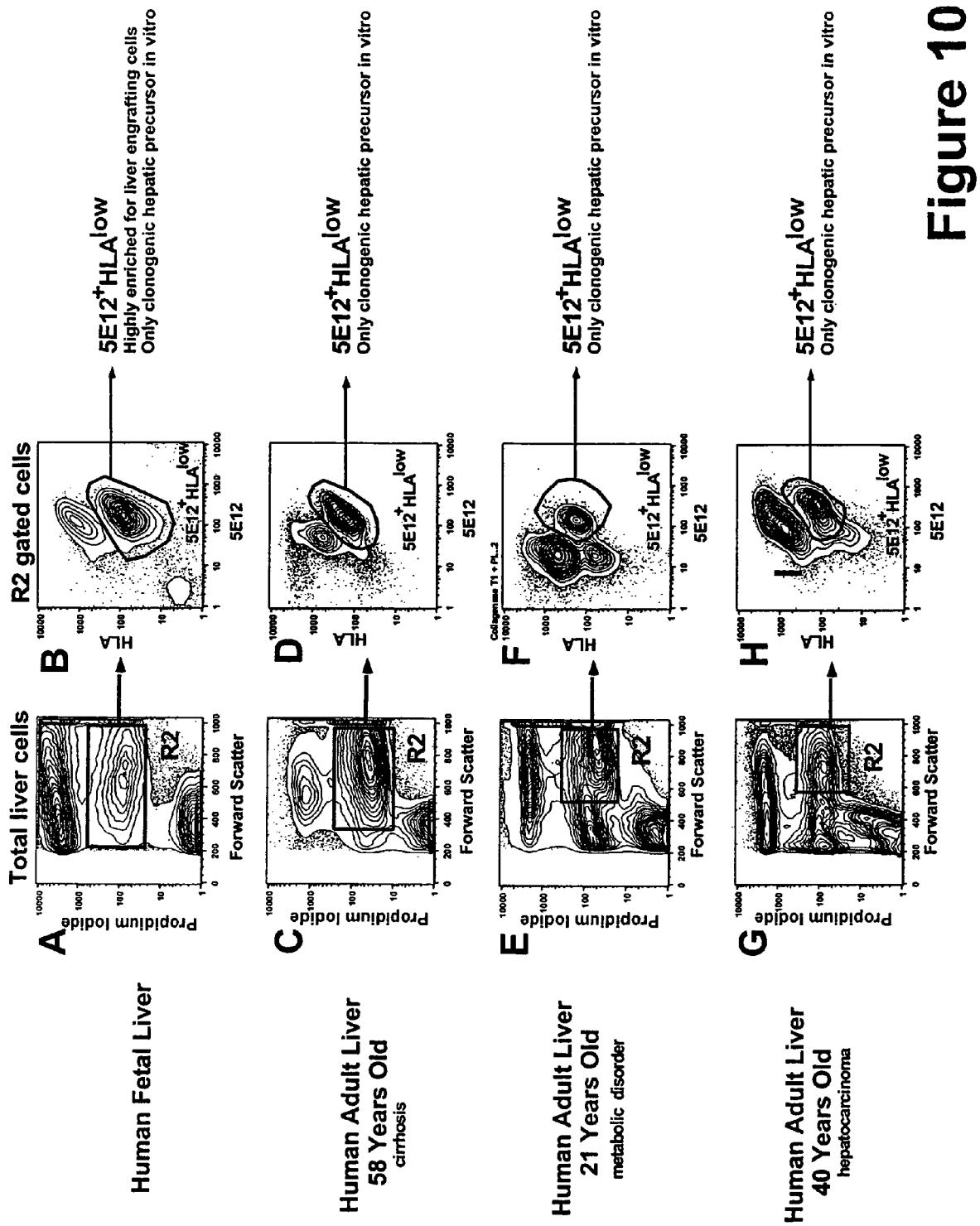

The data show (FIG. 3A) that CD14 does not stain the LEC cells (R2, 5E12$^+$ HLA$^{low}$). CD54, CD38 and CD34 positively stain the LEC (FIGS. 3B-3D). FIGS. 4A, 4D, 4G show the typical staining pattern for LEC. FIGS. 4B, 4E and 4H show that E-Cadherin, EpCam and CD49f have a staining profile similar to that of 5E12 on the R2 population. FIGS. 4C, 4F and 4I show that the LEC populations selected E-Cadherin, EpCam or CD49f are uniformly 5E12 positive. These data demonstrate that 5E12, E-cadherin, EpCam and CD49f can be used interchangeably in the selection of LEC. Similar data were obtained with adult liver tissue (shown in FIG. 9). FIG. 10 summarizes these data.

EXAMPLE 4

In Vitro Assay for Human Liver Cells

Liver cells, including liver progenitor cells, are shown to survive and proliferate on stromal cells used as feeders. The in vitro culture of these cells permits isolation and characterization of progenitor cells from liver. Two different feeder stromal cell lines were used as feeders, BMS-6, a bone marrow stromal line and FFS-1, a fetal fibroblast. This assay is based on a feeder cell dependent co-culture system and the nature of a liver progenitor cell which should be a highly proliferative cell with liver engrafting capability.

Materials and Methods

Feeder layer Preparation and Culture Conditions: FFS-1 murine fibroblast cells (derived from STO) were mitomycin treated (10 μg/ml, Sigma, St Louis, Mo.) for 5 hours and plated at 5×10$^4$ cells/cm$^2$. BMS-6 murine bone marrow stroma were plated at 1.6×10$^4$/cm. The feeder layers were cultured in 1:1 mixture of Dulbecco's modified Eagle's medium and Medium-199 with 10% FCS.

Isolation of Enriched Liver Cell Fractions using Flow Cytometry: Liver cell preparations were prepared by typical tissue digestion procedures and single cell suspensions and analyzed by multi-parameter flow cytometry. Isolation of specific liver cell subpopulations was accomplished using a fluorescence activated cell sorter (FACS™) manufactured by Becton Dickinson Immunocytometry Systems. Specifically, the FACSVantage SE is configured with argon, krypton, and Helium-Neon ion lasers, which deliver three spatially separate excitation sources. This setup allows us to employ a wide variety of commercially available fluorescent probes for the analyses of discrete cellular features. Specialized subsystems built into this instrument permit the indexed deposition of single cells directly into individual wells of tissue culture plates previously cultured with feeder layer cells. Computer assisted high-speed data acquisition systems allow the collection of up to nine independent data parameters from each single cell. The ability to collect listmode data files comprised of more than one million events facilitates the discrimination of very low frequency subpopulations. Data parameters were collected in the list mode data file and were analyzed by the software program Flowjo (www.Treestar.com). Pure populations of liver cells were sorted directly into individual wells of 96-well or 24-well plates previously cultured with feeder layer cells.

Protocol for freezing cells: Resuspend liver cells in IMDM+10% FCS with 40% FCS for 5 minutes on ice then mix 1:1 with IMDM+10% FCS with 15% DMSO. Freeze cells at −800 C than liquid nitrogen.

Protocol for hepatitis infection: Incubate liver cells with human serum containing hepatitis for an hour on ice, then plate the cells on stroma and culture the cells for 2 weeks.

Results

Figure 8:
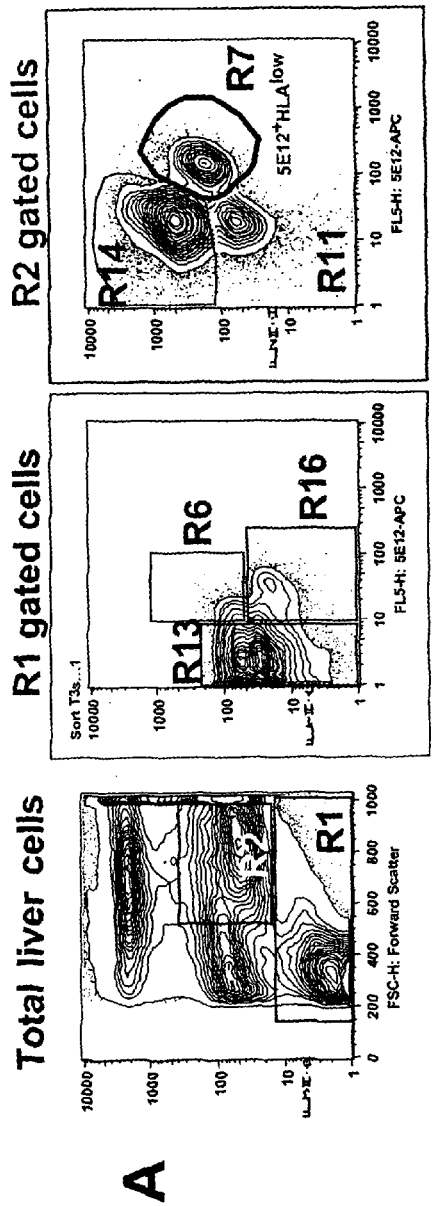
FIG. 8A shows the staining of human adult liver cells for the R1 and R2 populations; and the staining of the staining of the R2 population for 5E12, HLA.
FIG. 8B shows the expression of albumin and alpha-1 antitrypsin after culture in vitro.
Figure 8:
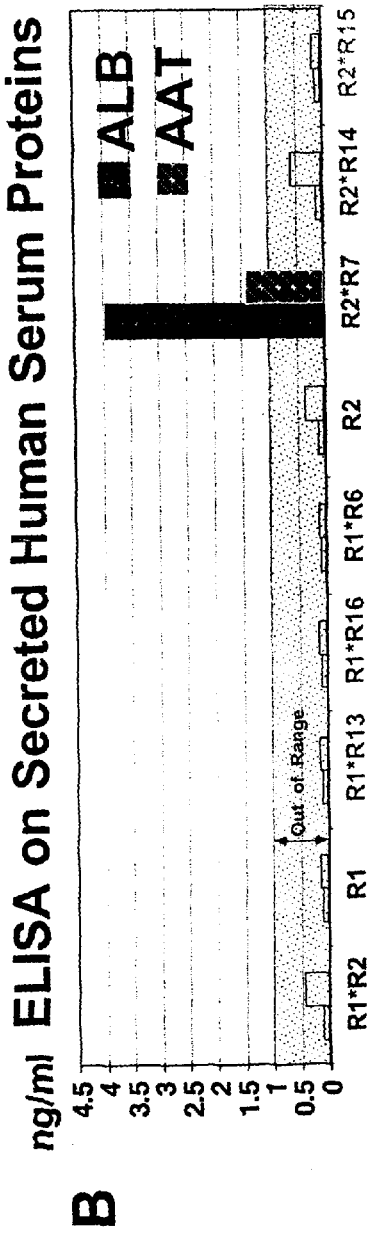

Liver cell populations were separated into R2/5E12+ versus R2/5E12− by MACS or sorting or both. The cells were then cultured for 2 weeks and then assessed the CFC-LBC (colony forming cell-liver bipotent colony) by the expression of Albumin and ck19 in the forming colonies, shown in FIG. 8. The hepatic colony frequency was calculated by limiting dilution using 3 different cell concentrations. The data is shown in Table 3, and FIG. 8 (human adult cells).

The limiting dilution assays can utilize a combination of cell sorting and ELISA to determine limiting dilutions. For example, cells were sorted according to R2 gates, expression of 5E12, and expression of HLA antigens. The sorted cells were diluted into 96 well plates as described above, and cultured in vitro for 14 days, then analyzed by ELISA for expression of alpha-fetoprotein, albumin, and alpha-1 antitrypsin.

EXAMPLE 5

In Vitro Model of Hepatitis Infection

A method is provided for the in vitro infection of hepatic colonies by hepatitis viruses. Fetal liver cells (18 g.w.) containing liver engrafting progenitor cells were isolated and infected with Hepatitis Virus D (HDV) and cultured for 2 weeks. Cells were cultured for two weeks, fixed and stained for albumin (APC-blue), Cytokeratin 19 (FITC-green) and HDV (PE-red) to identify hepatic progenitors infected with hepatitis D virus. Nuclei were counterstained with Hoechst.

Fetal liver cells were incubated with serum from patients infected with HDV virus. 1 hour later, the sample was put on stroma layer and left for 2 weeks. The culture was fixed and stained with hepatic and anti-HDV markers. These methods of culture support the growth of cells that are infectable with hepatitis viruses.

EXAMPLE 6

Ex vivo Expansion of Human Liver Engrafting Cell Populations

Human liver engrafting cells, which had been enriched for hepatocyte progenitors bearing the $HLA^{low}$ $5E12^+$ phenotype, were plated on or in an extracellular matrix (ECM) that provides for cellular attachment, adhesion, and proliferation. The cells were cultured in a suitable basal medium in combination with the matrix component laminin, in the presence of Liver engrafting cell (LEC) medium. The cell morphology is shown in FIG. 11.

Liver engrafting cell (LEC) Medium: DMEM/F12 (50:50) with L-glutamine; 10% fetal bovine serum; dexamethasone (10-7M); nicotinamide (10 mM); Beta-mercaptoethanol (0.05 mM); Penicillin/streptomycin (1×); Recombinant human hepatocyte growth factor (40 ng/mL); Recombinant human epidermal growth factor (20 ng/mL).

Throughout the course of ex vivo expansion, the clonogenic potential of expanded cells was assessed in a stromal coculture assay as described above for uncultured liver cells. The secreted hepatic proteins albumin, alpha-1-antitrypsin, or alpha-fetoprotein, were monitored by ELISA assays of culture supernatants from proliferating cells on ECM plus LEC medium or in stromal coculture.

Engraftment potential of cells expanded by culture on ECM plus LEC medium can be assessed by transplantation in various suitable animal models, including the NOD-SCID mouse or the NOD-SCID/FAH mouse. An additional approach is to induce differentiation of expanded cells as a means to promote improved liver engraftment or long-term hepatocyte function. Cells expanded by culture on ECM plus LEC medium may be exposed to additional growth factors, cytokines, or differentiation agents, to promote a differentiation state of a mature hepatocyte. The impact of such treatments on the engraftment potential of the expanded and differentiated cells can be evaluated by transplantation in animal models as described above.

EXAMPLE 7

Transplantation of Human Liver Engrafting Cell Populations

Figure 6:
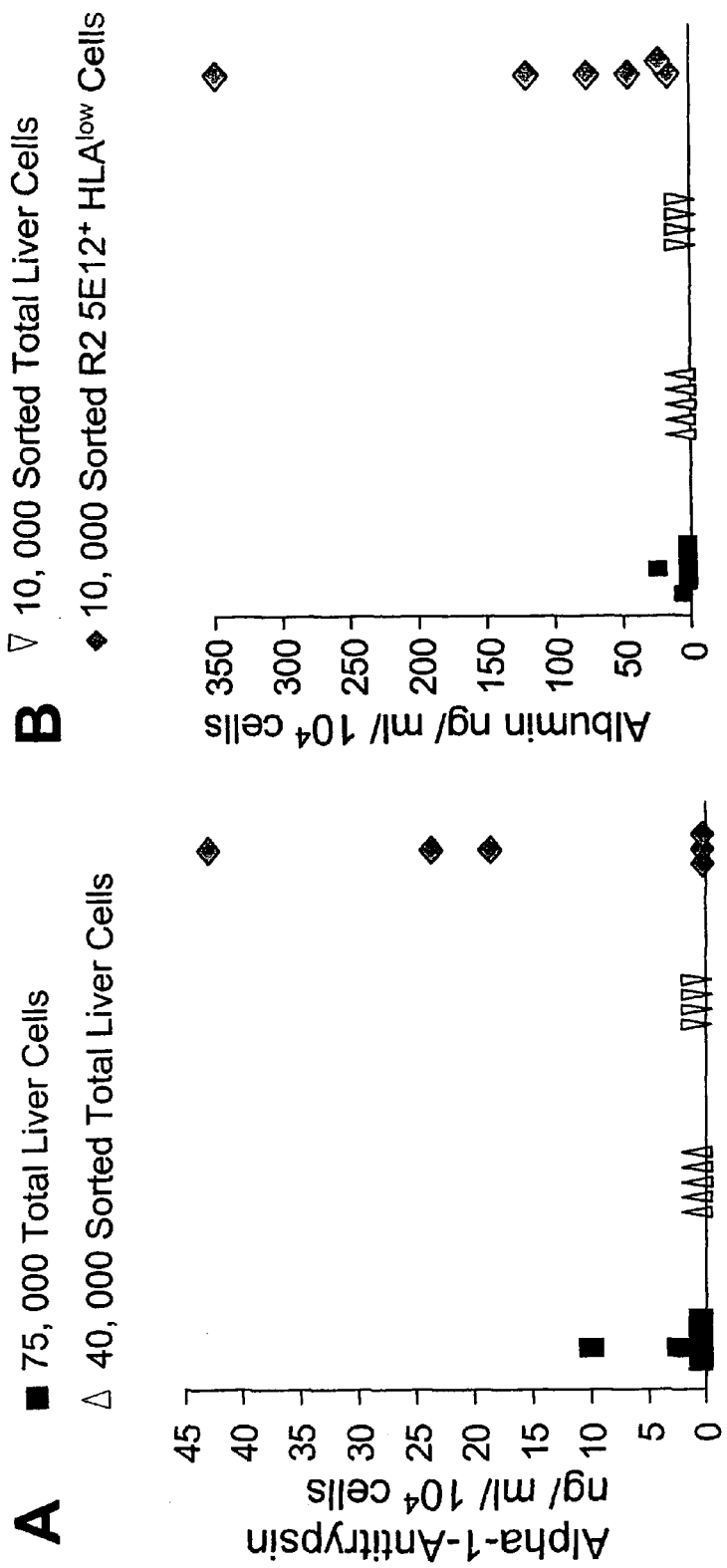
FIGS. 6A and 6B show the levels of circulating human alpha-1-antitrypsin (AAT)(9A) and albumin (ALB) (9B) protein from serum of NOD-SCID mice 6 weeks following transplantation of total liver cells, sorted total liver cells, or sorted R2 5E12$^+$ HLA$^{low}$ cells. The data demonstrate the engraftment and generation of functional hepatocytes from LEC.
Figure 7:
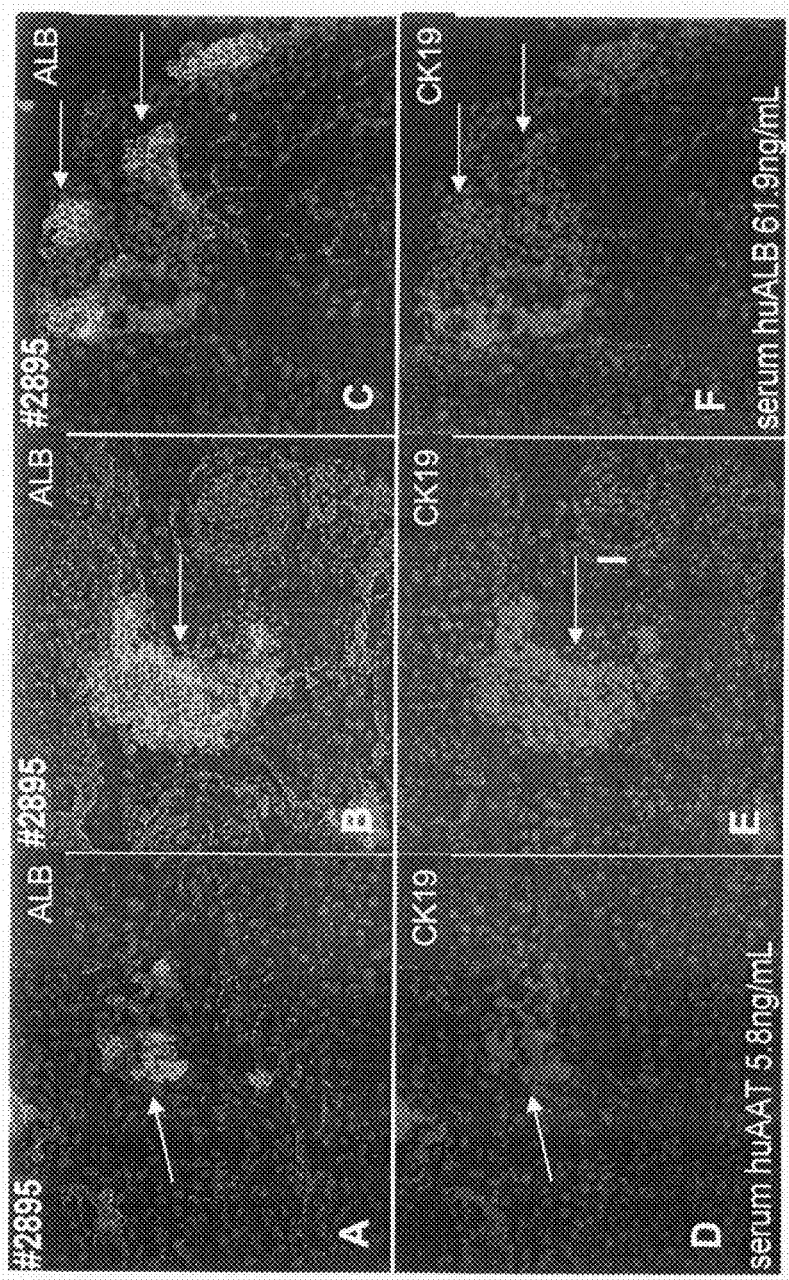
FIGS. 7A-7F show detection of human ALB or CK19 protein in engrafted human fetal liver cells within the liver of a NOD-SCID mouse 6 weeks following transplantation.

The engraftment and hepatocyte differentiation potential of human liver cells was assessed by transplantation into the NOD-SCID mouse. Briefly, human liver cells were resuspended in a injection buffer (50% Matrigel BD Biosciences #356234, 50% DMEM) and placed on ice until injection. Up to 20 microliters of cells in injection buffer were injected into the livers of 0-48 hours old newborn NOD-SCID mice. Serum from the injected mice was analyzed by ELISA 5-6 weeks after transplantation for the presence human liver-specific proteins (albumin, alpha-1-antitrypsin, or alpha-fetoprotein). In FIG. 6, circulating human alpha-1-antitrypsin (AAT) and albumin (ALB) protein was detected from serum of NOD-SCID mice 6 weeks following transplantation of total liver cells, sorted total liver cells, or sorted R2 $5E12^+$ $HLA^{low}$ cells. The levels of AAT or ALB in mice engrafted with 10,000 sorted R2 $5E12^+$ $HLA^{low}$ cells was greater than or equal to that in mice engrafted with 75,000 unsorted total liver cells, or 10,000 or 40,000 sorted total liver cells. The human AAT or ALB are repeatedly detectable in mice transplanted with sorted R2 $5E12^+$ $HLA^{low}$ cells for up to 5 months, indicating a durable engraftment and sustained hepatic differentiation. FIG. 7 shows detection of human ALB or CK19 protein in engrafted human fetal liver cells within the liver of a representative NOD-SCID mouse 6 weeks following transplantation. The serum levels of human AAT and ALB detected by ELISA analysis at the time of sacrifice are shown in the bottom panels.

What is claimed is:

1. A composition of adult human liver engrafting cells isolated from adult liver tissue, wherein at least 50% of the cells in said composition are each $HLA^{low/neg}$; are $5E12^+$; and express albumin; wherein said $HLA^{low/neg}$, $5E12^+$, and albumin expressing cells in said composition give rise to mature hepatocytes.

2. The composition of claim 1, wherein the at least 50% of the cells in said composition are also negative for CD117 and CD14.

3. The composition of claim 1, wherein the at least 50% of the cells in said composition are also positive for at least one marker selected from the group consisting of Ep-Cam, E-Cadherin, CD49f and CK19.

4. The composition of any one of claim 1, 2, or 3 wherein said adult human liver engrafting cells are genetically modified to comprise an exogenous DNA vector.

* * * * *